(12) United States Patent
Doubler et al.

(10) Patent No.: US 9,649,142 B2
(45) Date of Patent: May 16, 2017

(54) MODULAR HEAD ASSEMBLY (71) Applicant: Spinal LLC, Palm Beach Gardens, FL (US)

(72) Inventors: Robert L. Doubler, Monroe, MI (US); John E. Hammill, Sr., Maumee, OH (US)

(73) Assignee: Spinal LLC, Palm Beach Gardens, FL (US)

( * ) Notice: Subject to any disclaimer, the term of this patent is extended or adjusted under 35 U.S.C. 154(b) by 0 days.

(21) Appl. No.: 14/643,448

(22) Filed: Mar. 10, 2015

(65) Prior Publication Data
US 2016/0262816 A1 Sep. 15, 2016

(51) Int. Cl.
*A61B 17/86* (2006.01)

(52) U.S. Cl.
CPC .. *A61B 17/8605* (2013.01); *A61B 2560/0443* (2013.01)

(58) Field of Classification Search
CPC .............................. A61B 17/86; A61B 17/8605
USPC ............................ 606/60, 246–279, 300–331
See application file for complete search history.

(56) References Cited

U.S. PATENT DOCUMENTS

| 5,545,165 | A | 8/1996 | Biedermann et al. |
|---|---|---|---|
| 5,584,834 | A | 12/1996 | Errico et al. |
| 5,628,740 | A | 5/1997 | Mullane |
| 5,725,527 | A | 3/1998 | Biedermann et al. |
| 5,879,350 | A | 3/1999 | Sherman et al. |
| 6,050,997 | A | 4/2000 | Mullane |
| RE37,665 | E | 4/2002 | Ralph et al. |
| 6,371,957 | B1 | 4/2002 | Amrein et al. |
| 6,478,798 | B1 | 11/2002 | Howland |
| 6,565,565 | B1 | 5/2003 | Yuan et al. |
| 6,610,062 | B2 | 8/2003 | Bailey et al. |
| 6,610,063 | B2 | 8/2003 | Kumar et al. |
| 6,613,050 | B1 | 9/2003 | Wagner et al. |
| 6,626,906 | B1 | 9/2003 | Young |
| 7,105,029 | B2 | 9/2006 | Doubler et al. |
| 7,118,303 | B2 | 10/2006 | Doubler et al. |
| 7,334,961 | B2 | 2/2008 | Doubler et al. |
| 7,335,201 | B2 | 2/2008 | Doubler et al. |
| 7,438,715 | B2 | 10/2008 | Doubler et al. |
| 7,658,582 | B2 | 2/2010 | Doubler et al. |
| 7,678,138 | B2 | 3/2010 | Fitts et al. |
| 7,862,281 | B2 | 1/2011 | Doubler et al. |
| 7,981,143 | B2 | 7/2011 | Doubler et al. |
| RE42,715 | E | 9/2011 | Sones |
| 8,814,919 | B2 * | 8/2014 | Barrus ............... A61B 17/7037 606/266 |
| 2008/0243193 | A1 * | 10/2008 | Ensign ............... A61B 17/7032 606/305 |
| 2012/0041490 | A1 * | 2/2012 | Jacob ................. A61B 17/7032 606/264 |

* cited by examiner

*Primary Examiner* — Christopher Beccia
(74) *Attorney, Agent, or Firm* — McHale & Slavin, P.A.

(57) ABSTRACT

A low profile orthopedic device is used to fix and stabilize bones to correct anomalies in skeletal structure occurring naturally or by trauma. Bone screws are screwed into bones by application of torque. Connectors are attached to the anchored bone screws. Each connector includes a clamp and a compression ring. A connecting rod connects several connectors together. The clamps are tightened to hold the rod to the bone screws in a pre-selected position by linear movement of the compression ring.

15 Claims, 5 Drawing Sheets

MODULAR HEAD ASSEMBLY

FIELD OF THE INVENTION

This invention relates to orthopedic surgery and, in particular, to a bottom loading modular head assembly.

BACKGROUND OF THE INVENTION

Chronic back problems are caused by intervertebral disc disease and deterioration and loss of stability of the intervertebral joints. Examples of these spinal conditions include degenerative disc disease, scoliosis, spondylolithesis, spinal stenosis, etc. Stabilization and/or arthrodesis of the intervertebral joint can reduce the pain associated with movement of a diseased or deteriorated intervertebral joint. In order to allow for development of a solid intervertebral fusion, the spine has to be stabilized. Severe trauma to the back can further cause conditions wherein the spine needs to be stabilized. There are many instances in which it is necessary to stabilize and fix bones and bone fragments in a particular spatial relationship to correct the location of skeletal components due to injury or disease. One group of devices employ a number of bone screws placed across a discontinuity in adjacent vertebrae and connected by a rod to maintain a predetermined spatial location.

Spinal stabilization systems have been developed to stabilize the vertebrae to allow for fusion or stabilization of diseased intervertebral joints. One type of spinal stabilization system includes connectors and rods that are used to stabilize the spine. Some examples of such spinal stabilization systems are disclosed in U.S. Pat. Nos. 6,613,050; 6,371,957; 6,050,997; 5,879,350; 5,725,527; 5,628,740; and 5,545,165, the disclosures of which are incorporated herein by reference. In these systems, connectors are anchored to the vertebral bodies desired to be stabilized by anchoring structures such as screws or hooks. One or more connecting rods are then secured to the connectors to form a connector/rod construct that stabilizes the vertebral bodies to which the connectors are secured.

In many known stabilization systems, threaded nuts are used to secure the rods to the connectors. The rods can be provisionally held in position by loosely tightening the nuts on the connectors. After desired adjustments are made with respect to the relative positioning of the bones desired to be stabilized, the nuts can be further tightened to finally secure the connector/rod construct. Typically, a torque wrench or similar device is used to achieve the required torques to finally secure the connector/rod construct. To prevent torque from being transferred to the patient while tightening the nut, an anti-torque device is frequently used in combination with the torque wrench. The effective use of the torque wrench and anti-torque device can be difficult and often is dependent upon the strength and experience of the surgeon. The inventors torqueless fasteners patents include U.S. Pat. Nos. 7,105,029; 7,118,303; 7,334,961; 7,335,201; 7,438,715; 7,658,582; 7,678,138; 7,862,281; 7,981,143 and RE42,715, the entire disclosures of which are incorporated herein by reference.

U.S. Pat. No. 6,626,906 issued Sep. 30, 2003 to Young teaches a spinal rod attached to a spinal anchor by a clamp. The clamp is tightened about the anchor by a collet screwed into the clamp. The rod is held in the clamp by a split ring that is reduced in size by the collet. The anchor is placed in the bone by torque and the collet is tightened by additional torque.

U.S. Pat. Nos. 6,610,063; 6,610,062; 6,565,565; RE 37,665; 6,478,798; 5,584,834 teach various spinal rod coupling devices that are secured to bone screw anchors by clamps that require additional torque to be applied to the assembly after the bone screw has been seated in the bone.

In normal practice, the bone screws are each anchored in the bone with a specific amount of torque that approaches the ultimate sustainable force between the screw threads and the bone. The bone screws are then connected together by a rod having sufficient stiffness to maintain the desired skeletal orientation. The connection between the rod and the bone screws must be strong enough to be immobile. Alternatively, a torqueless connector is coupled to a bone screw, wherein the bone screw is installed in combination with the connector.

All these spinal fixation devices result in additional torque applied to the assembly, and thereby to the bone screw, to tighten and lock the rod to each of the bone screws. The additional load may strip the purchase between the bone and the threads of the bone screw. To prevent such a result, some tool must be used to counter the torque of locking the rod and the screws. The use of an anti-torqueing tool requires additional coordination by the surgeon or surgeons to prevent slippage.

SUMMARY OF THE PRESENT INVENTION

In particular, the present invention provides a linear locking set screw system capable of rapid linear engagement of a bone screw and a rod. Bone screws are screwed into bones by application of torque, the top of each bone screw having a spherical head. A connector is attached to the head of each of the anchored bone screws. Each connector includes a clamp body having a rod slot section, a receptacle section for placement over the spherical head and a pin retention slot for stabilizing and immobilizing the assembly once it has been installed in a subject. A compression ring is placed around the clamp body. A connecting rod connects several connectors together upon placing the rod within the rod slot. The clamps are tightened to hold the rod to the bone screws in a pre-selected position by linear movement of the compression ring.

It is an objective of the present invention to provide a low profile spinal stabilization system capable of precise and reproducible linear engagement and disengagement.

Still another objective of the present invention is to provide a connector that provides a bottom loading low profile spinal stabilization system, the connector being attached to a bone screw after the bone screw has been anchored.

Yet another objective of the present invention is to provide a low profile spinal stabilization system capable of locking a spinal connecting rod to an anchored bone screw by linear engagement so as to eliminate torque fastening.

Yet a further objective of the present invention is to teach the use of a linear fastener that is adjoined to an anchored bone screw for support of ancillary devices adapted to be secured together without rotational torque forces.

Other objectives and advantages of this invention will become apparent from the following description taken in conjunction with the accompanying drawings which set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figures 1, 2:
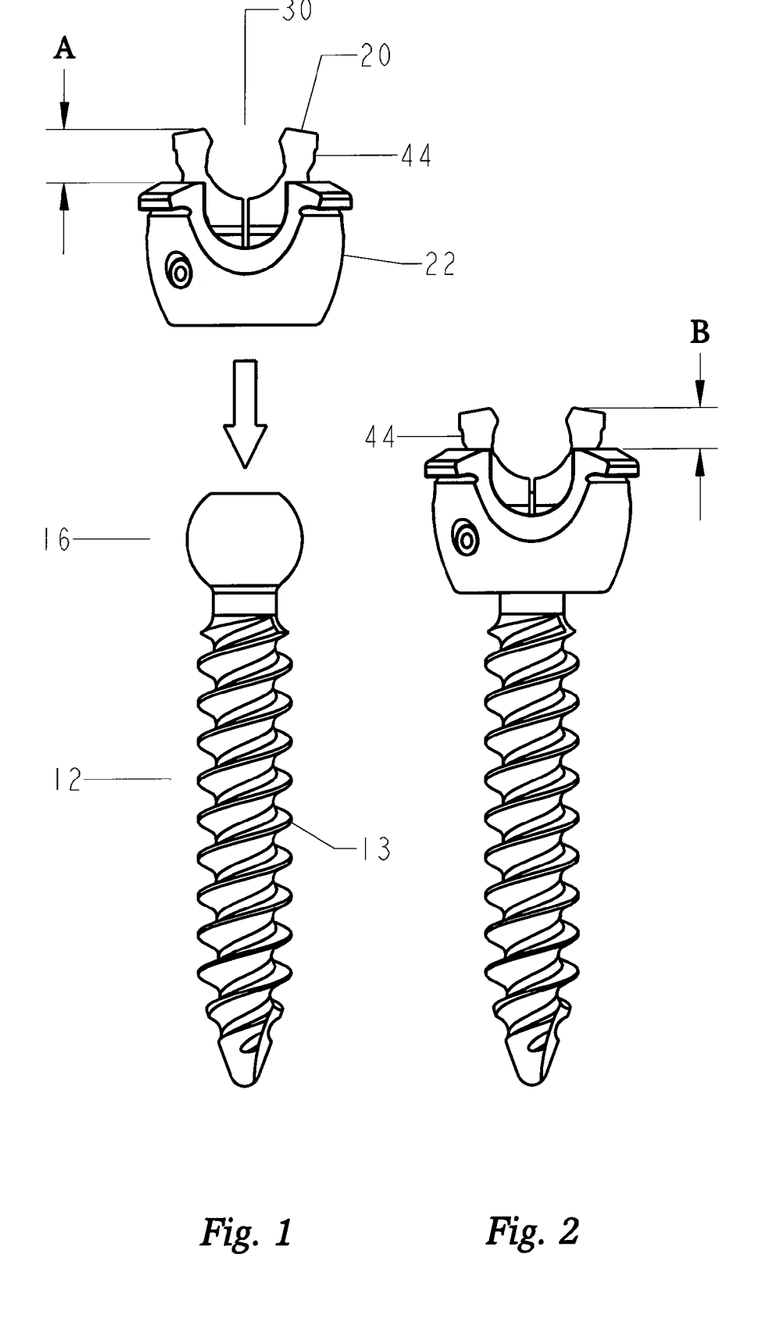
FIG. 1 is an exploded view of the bottom loading orthopedic device of the instant invention.
FIG. 2 is a plane view of the device with the connector coupled to the bone screw.
Figures 3, 4:
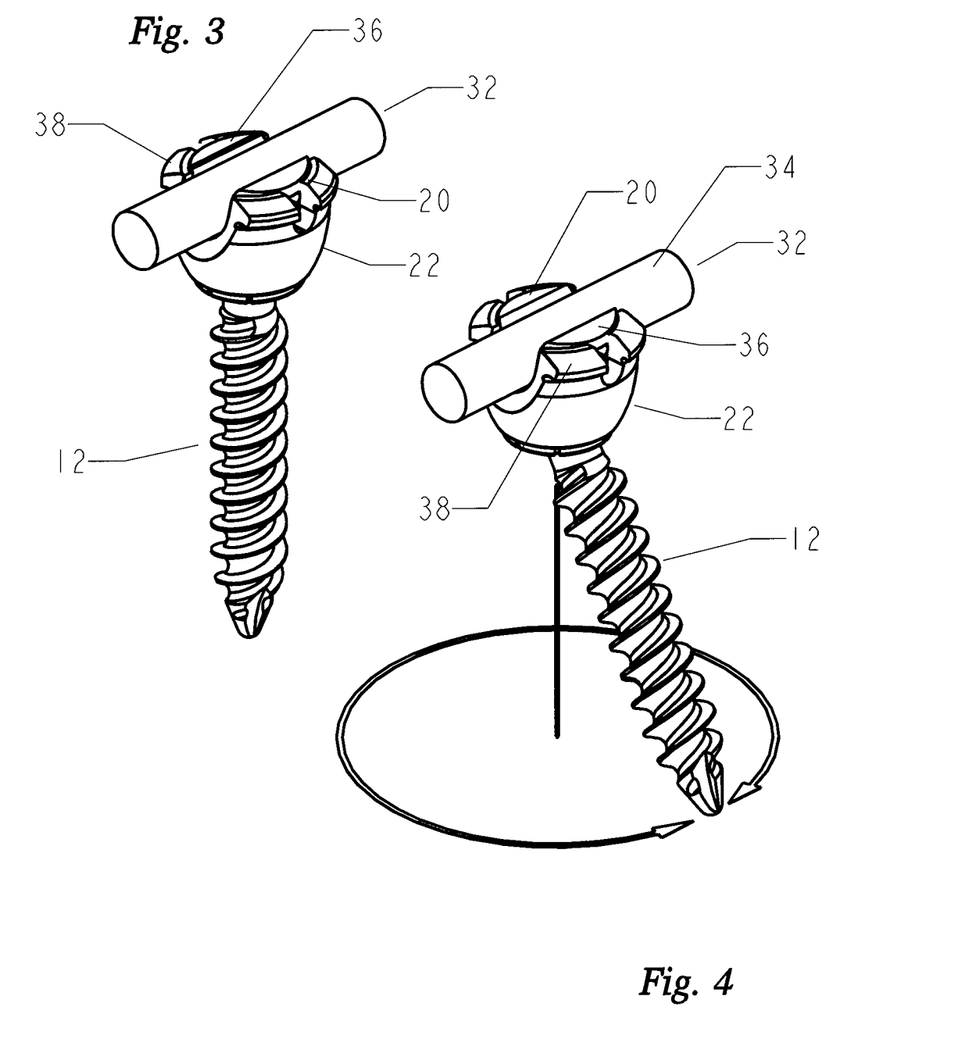
FIG. 3 is a plane view of the device locked to a rod providing a vertical low profile vertical stance.
FIG. 4 is a plane view of the device locked to a rod providing an angular low profile stance.
Figure 5:
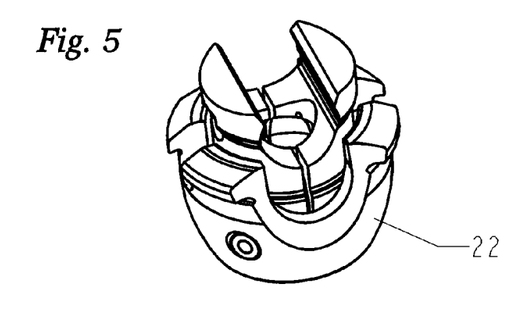
FIG. 5 is a perspective view of the connector.

Referring now to the Figures, set forth is an orthopedic fixation device 10 for use in stabilizing and fixing the vertebra in relation to each other and the sacrum. The fixation device 10 employs a bone screw anchor 12 having an exterior helical threaded shank 14 to gain purchase in the cancellous bone through application of torque. A spherical head 16 is formed at the top of the helical threaded shank 14 which is constructed and arranged for bottom loading into a connector 19 formed from a clamp 20 positioned within compression ring 22. A recess 24 is formed in the top of the bone screw anchor 12 to permit installation of the bone screw anchor into cancellous bone by rotation. A torque is applied to the bone screw anchor by the surgeon using a tool (not shown) that engages the recess 24 in the head 16 and rotates the screw about its longitudinal axis. The amount of torque is critical to installation and the long life of the prosthesis in that too little does not secure the screw from loosening or backing out, and too much causes the stripping of the thread path in the bone and loss of purchase. The surgeon attempts to apply the optimum torque when placing the screws in the bone and additional torque on the bone screw is to be avoided. FIG. 1 illustrates an exploded view with the bone screw anchor 12 of head 16 exposed and available for receipt of the clamp 20 and compression ring 20. FIG. 2 illustrates the bone screw anchor 12 upon receipt of the clamp 20 and compression ring 22, a rod slot 30 is available for receipt of a rod. As illustrated, a first position is formed wherein the clamp 20 is placed over the spherical ball 16 and is available for receipt of a rod into the rod slot 30. The spherical ball 16 is frictionally engaged by a lower end of the clamp 20, to be further explained later in this specification, providing a sufficient interference fit to maintain the rod slot 30 in a position that can be directed by the surgeon awaiting receipt of the rod. FIG. 3 illustrates the bone screw anchor 12 in a vertical stance with a rod 32 placed within the rod slot 30 and the clamp 20 drawn into the compression ring 22, locking the rod 32 in fixed position in relation to the bone screw anchor 12. FIG. 4 illustrates the bone screw anchor 12 in an angular stance with a rod 32 placed within the rod slot 30 and the clamp 20 drawn into the compression ring 22, locking the rod 32 in fixed angular position in relation to the bone screw anchor 12. The spherical head 16 of the bone screw anchor 12 provides polyaxial movement of the clamp 20 and compression ring 22. During the spinal fixation, several bone screw anchors are threaded into the different vertebrae according to the anatomy of each vertebra. This results in a series of bone screw anchors without uniformity in angle or alignment. To compensate for these anomalies, the connection between the head of the screw anchors and the clamp bodies pivots or swivels to capture a connector rod. FIGS. 3 and 4 illustrate how the screw anchors can be positioned in relation to the clamp bodies. Further, the low profile stance is illustrated wherein the upper edge 34 of the rod 32 is locked in a position wherein the clamp top or proximal surface 36 is in a similar plane as the compression ring top or proximal surface 38.

Figure 6:
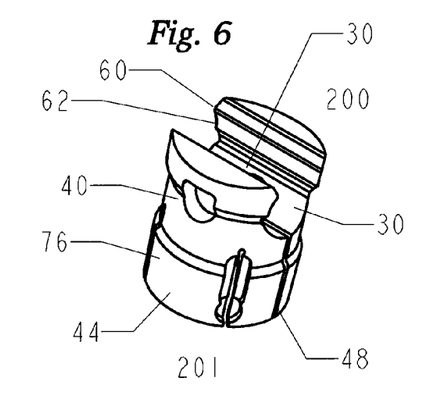
FIG. 6 is an upper perspective view of the clamp portion of the connector.
Figure 7:
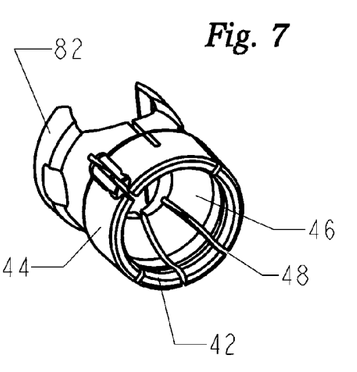
FIG. 7 is a lower perspective view of FIG. 6.
Figure 8:
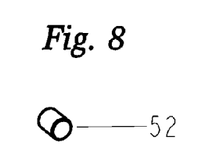
FIG. 8 is a perspective view of a pin used to secure the clamp to the compression ring.
Figure 9:
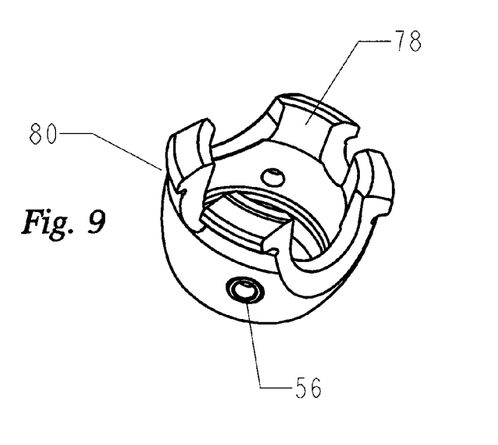
FIG. 9 is an upper perspective view of the compressing ring portion of the connector.
Figure 10:
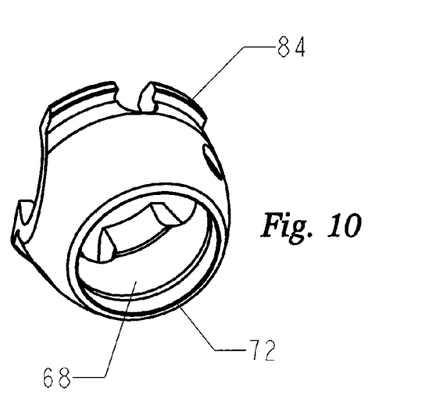
FIG. 10 is a lower perspective view of FIG. 9.

The clamp body 20, illustrated in greater detail in FIGS. 6 and 7, is generally tubular comprising a proximal end 200 and a distal end 201, the proximal end 200 defined by a U-shaped opening or rod slot 30 for receipt of a rod and the distal end 201 defining an annulus. The generally tubular arrangement of the clamp body 20 forms a receptacle section 42 at the distal end 201 and a rod slot 30 at the proximal end 200. The receptacle is of a size to accommodate the head 16 of the bone screw anchor with a wall 40 formed by an outer wall surface 44 having a cylindrical shape and an inner wall surface 46 of a conical shape for capturing the head 16 upon insertion. A series of circumferential slots and relief slits are constructed and arranged to increase the radial flexibility of the wall 40 along the receptacle section 42 in response to the curvature of the compression ring 22. The slot 30 has an upper longitudinal ridge 60 and a lower longitudinal ridge 62 to grip the connector rod 32. In some embodiments the clamp 20 comprises a lip is formed along the lower edge of the receptacle section 42 outer wall surface 44. The outer wall surface 44 of clamp 20 may be tapered or otherwise shaped to provide a change in external diameter along the length.

The clamp body 20 further comprises a pin receiving slot 100 constructed and arranged to receive a pin 52. During installation, the clamp 20 captures the head 16 of the shank and the pin 52 prevents movement of the installed bone screw.

The compression ring 22 is force fit on the wall 40 of the clamp 20 by flexing the tubular walls. The compression ring 22 is movable along the outer surface wall 44 from an open position to a closed position. The open position, as shown in FIG. 2, allows swiveling movement of the bone screw anchor head 16 and sliding movement of the connector rod 32 within the clamp 20. In the closed position, shown in FIGS. 3 and 4, the compression ring 22 applies compressive forces between the clamp 20 and the rod 32, and between the clamp 20 and the bone screw anchor 12. The compression ring 22 has a shaped inner surface 68 with a lower annular ridge 72 and an upper annular ridge which engages the annular bulge 76, on the outer wall surface 44 of the clamp 20 in the closed position. In addition, the compression ring 22 includes an annular surface 78 formed along compression fingers 80 for engaging the upper bulge 82 formed along the outer side surface of the clamp in the closed position. The clamp 20 is preinstalled in the compression ring 22 and a pin 52 is placed within receptacle 56 of the compression ring 22 to maintain the clamp within the compression ring. The pin operates as an interference fit to prevent the clamp 20 from disengaging the compression ring 22 while the head 16 of the bone screw anchor is installed.

Figure 11:
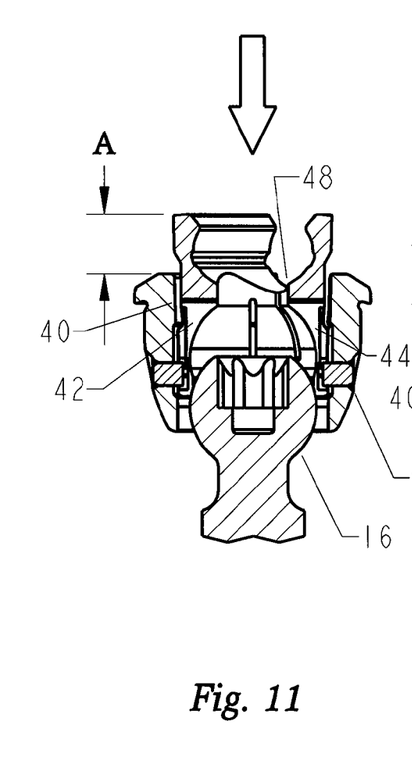
FIG. 11 is a cross sectional view of the connector before attachment to a bone screw.
Figure 12:
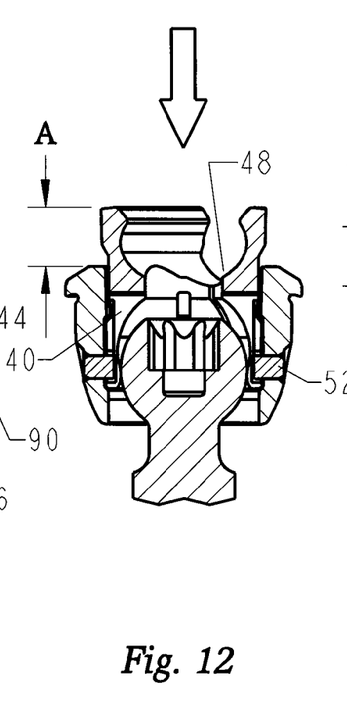
FIG. 12 is a cross sectional view of the connector during attachment to the bone screw.
Figure 13:
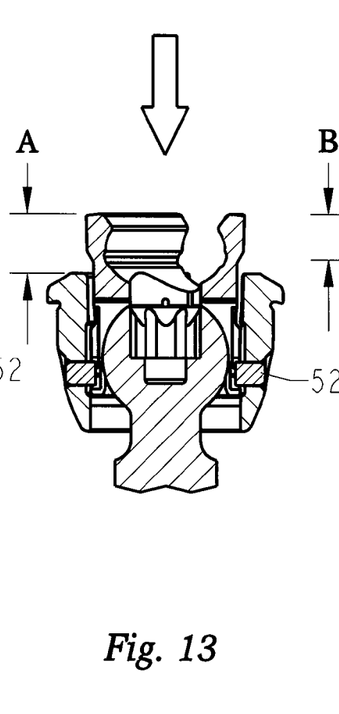
FIG. 13 is a cross sectional view of the connector after attachment to the bone screw.

FIGS. 11 to 14 illustrate the shank capture sequence. FIG. 11 depicts the clamp body 20 assembled to the compression ring 22. The clamp body 20 is shown making the initial contact with the spherical head 16, the receptacle section 42 is available for receipt of the head 16. The receptacle section 42 includes the wall 40 having a cylindrical shaped outer wall surface 44 that is enlarged along a length and expandable into an inner wall surface 90 of the compression ring 22. FIG. 12 depicts the clamp body capturing the head 16 at the maximum diameter of the head 16, the clamp body being at its most expanded position. The series of circumferential slots and relief slits 48 increase the radial flexibility of the wall 40 along the receptacle section 42 in response to the curvature of the head 16 as it pushes apart the circumferential slots and relief slits 48 of the clamp body 20 into the inner wall surface 90 of the compression ring 22. FIG. 13 depicts the fully captured spherical head 16 by the clamp body 20. The head 16 is shown within the receptacle section 42, the wall 40 now encompasses the head 16 with the outer wall surface 44 restored to a biased position around the head 16. The rod slot 30 is now available for positioning by the surgeon, the head 16 is in frictional contact with the clamp 20 wherein the clamp 20 can be placed in any angular position and held in position for receipt of a rod. Once a rod is inserted into the rod slot, the compression ring 22 is lifted up while the clamp 20 is pushed down to provide a low profile locked rod as illustrated in FIGS. 3 and 4. The pins 52 have moved into the pin shaft or passageway and prevent any further movement of the clamp.

Figure 15:
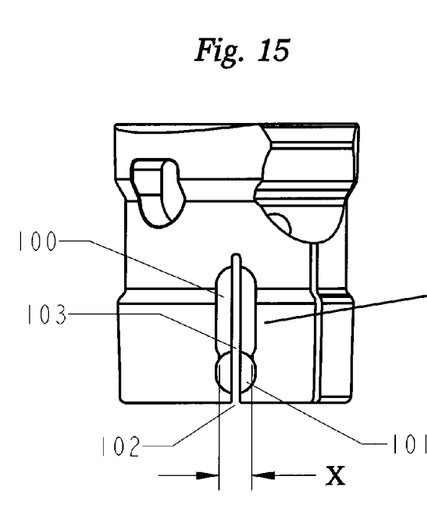
FIG. 15 is a side view of the clamp body showing a pin retention slot.
Figure 16:
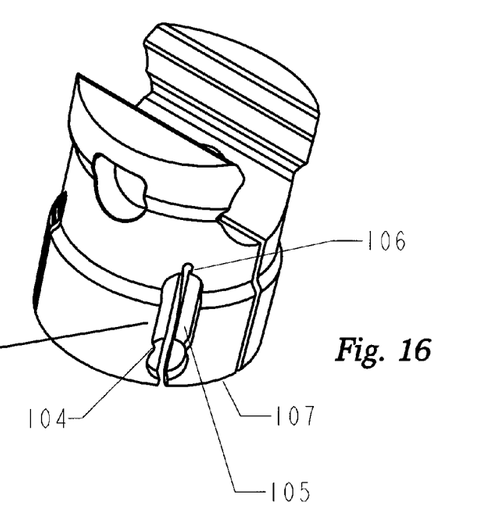
FIG. 16 is a perspective view of FIG. 15.
Figure 17:
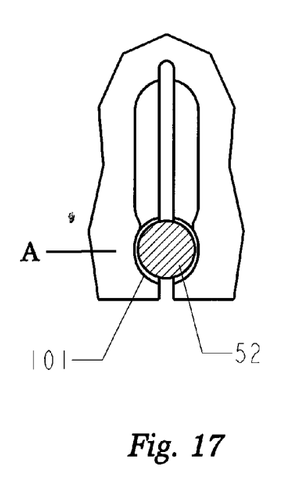
FIG. 17 is a side view of the clamp body showing a pin retention slot with a pin inserted therein.
Figure 18:
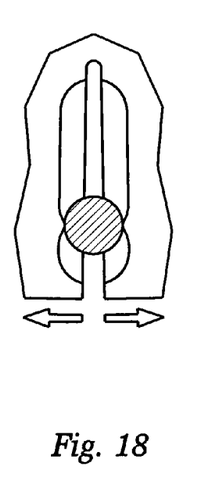
FIG. 18 is a side view of the clamp body showing the pin in the pin retention slot moving up past the lip portion.
Figure 19:
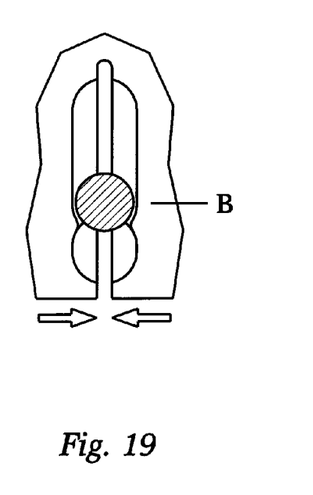
FIG. 19 is a side view of the clamp body showing the pin moving up into the pin shaft or passageway during installation of the instrument.

FIGS. 15 and 16 depict the clamp body 20 showing the pin retention slots 100. The pin retention slots 100 comprise a pin receiving portion 101 constructed and arranged to receive a pin 52. The pin receiving portion 101 is generally an open circle having an expansion slot 102 at the distal end of the pin receiving portion 101 and an opening 103 at the opposing end or apex of the pin receiving portion 101 to form a lip 104. The lip 104 allows the uni-directional movement of the pin 52 past the lip 104 and into the shaft or passageway 105. The shaft 105 comprises an expansion slot 106 at apex of the shaft or passageway, directly opposite and linearly disposed from the expansion slot 102 defined at the distal end 107 of the clamp 20. The shaft or passageway can be of various lengths to allow variable positioning of the pin 52 during installation. These features and the movement of the pin 52 during installation of the assembly are shown in greater detail in FIGS. 17, 18 and 19. FIG. 17 shows the pin 52 inserted into the pin receiving portion 101 of the pin retention slot 100. In this position, the pin 52 has been inserted through the pin aperture 56 of the compression ring 22 and the pin receiving portion 101 of the clamp body 20. In this position the head 16 is at the first or open position allowing for the insertion of the shank 12, and the capturing of the head 16. This position corresponds to a first or open position depicted in FIG. 11. As the clamp body 20 is pushed downwards to capture the head 16, the clamp body 20 expands over the head 16 and the pin 52 moves upwards through the lip 104 as depicted in FIG. 18. Sufficient force is applied as the clamp 20 passes over the head 16 and the expansion slot 102 allows for flex of motion so that the pin 52 can pass through the lip 104. As the head 16 is captured, the compression ring 22 applies compressive forces between the clamp 20 and the bone screw anchor 12. Since the diameter of the lip portion 104 is now constricted in size, this prevents the pin 52 from re-entering the pin receiving portion 101 of the pin retention slot 100m as shown in FIG. 19.

The application of the compressive force that immobilizes the components of the orthopedic device is generated by a linear movement of the compression ring relative to the exterior walls of the clamp. This movement to the closed position is accomplished using a simple telescoping instrument engaging the clamp 20 and the compression ring 22 so that equal and opposite forces move the ring without imparting stress to the anchored screw. The instrument includes an inwardly facing lip for engaging an outwardly projecting tab to pull up on the compression ring at the same time an insertion tap places an equal and opposite force onto the rod, forcing the clamp 20 into the compression ring 22 for locking the rod and bone screw anchor in position. In the event of remedial surgery, the clamp may be moved to the open position in the same manner.

Figure 14:
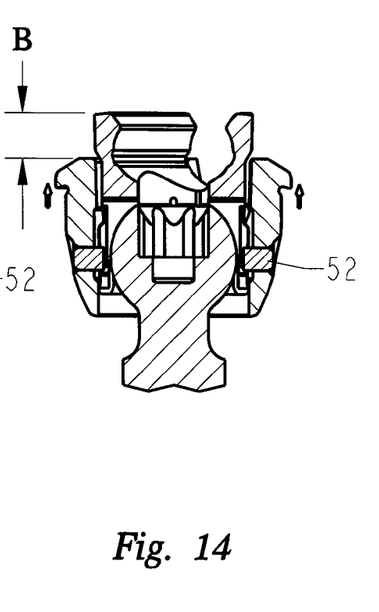
FIG. 14 is a cross sectional view of the connector in locked or closed position.

The instant invention provides an orthopedic kit for stabilizing bones. The kit comprises at least one bone screw having a first end constructed and arranged as a shank portion 13 for penetrating securement to a bone and a second end constructed and arranged as a head portion 16. The connector 19 is used for securing a rod to a plurality of anchored bone screws, the connector 19 is formed from a clamp universally connected to the head portion 16 of each anchored bone screw 12 for securing the anchored bone screw to a rod 32. The clamp 20 has an elongated body with an exterior wall 40 with a first annular bulge 76, a pin retention slot 100, and a rod slot 30 extending across the exterior wall constructed and arranged to slidably accept the rod 32. A compression ring 22 surrounding the exterior wall of the clamp 20, the compression ring linearly traversable along the exterior wall 40 between a first position and a second position by a force consisting of a linear force along a longitudinal axis of the clamp 20; the first position permitting adjustment of the rod as depicted in FIGS. 2 and 13, and the second position compressing the clamp 20 to immobilize the rod 32 with respect to the bone screw 12 as illustrated in FIGS. 3, 4 and 14. Traversal of the compression ring 22 from the first position to the second position causes the compression ring 22 to cooperate with the annular bulge 76 to apply compressive forces to the clamp 20 to immobilize the connections between the clamp 20 and the rod 32, and the clamp 20 and the anchored bone screw 12. The annular bulge 76 is positioned along a length of the exterior wall 40 of the clamp thereof to provide a change in the external diameter of the clamp; the annular bulge 76 constructed and arranged to cooperate with the compression ring 22 to apply compressive forces to the clamp 20 for immobilizing the connections between the clamp and the anchored bone screw head 16.

The exterior wall 40 of the clamp 20 includes a second bulge 82 to provide a change in the external diameter along the upper edge of the exterior wall. The annular bulge is constructed and arranged to cooperate with the compression ring 33 to apply compressive forces to the clamp 20 for immobilizing the connections between the clamp and the rod using ridges 60 and 62 for additional compressive force.

The first bulge 76 is constructed and arranged to cooperate with a lower annular ridge 72 while the compression ring 22 is in the second position to immobilize the connection between the clamp 20 and the anchored bone screw head 16.

The clamp 20 further comprises at least one pin retention slot 100. The pin retention slots 100 comprise a pin receiving portion 101 constructed and arranged to receive a pin 52. The pin receiving portion 101 is generally an open circle having an expansion slot 102 at the distal end of the pin receiving portion 101 and an opening 103 at the opposing end or apex of the pin receiving portion 101 to form a lip 104. The lip 104 allows the uni-directional movement of the pin 52 past the lip 104 and into the shaft or passageway 105. The shaft 105 comprises an expansion slot 106 at apex of the shaft or passageway, directly opposite and linearly disposed from the expansion slot 102 defined at the distal end 107 of the clamp 20. The shaft or passageway having varying lengths to allow variable positioning of the pin 52 during installation.

A method is further disclosed of using the orthopedic device to stabilize bones across a discontinuity. The method comprises providing at least two bone screws 12 having a threaded shaft 14 and a spherical head 16; anchoring the bone screws 12 into a bone by rotation of each screw 12 into the bone; providing a connector having a clamp body 20 and a compression ring 22. The clamp body 20 has a spherical head receptacle 42 at one end and a rod slot 30 at an opposing end, the receptacle sized to accommodate the head of the bone screw 16. The compression ring 22 has an interior wall 68 movable along an exterior wall 44 of the clamp body 20 between an open position and a closed position. The compression ring also includes an annular flange 84 at the upper edge thereof and an aperture 56 for receipt of a pin, the pin aperture 56 situated in alignment with the pin receiving slot 101 of the clamp 20. The open position is defined when the compression ring 22 is adjacent to the receptacle 42 such that the bone screw 12 is pivotable relative to the clamp body 20. A rod member slot 30 is placed whereby the rod member extends across a discontinuity; and repositioning the compression ring from its open position to its closed position by applying a linear force along the longitudinal centerline of the clamp 20 for traversing the compression ring 22 to a closed position along the exterior wall 44 of the clamp member 20 to compress the clamp member and prevent the pin 56 from moving. This motion substantially fixes the clamp member 20 and the rod member in a predetermined orientation with respect to the anchored bone screw 12 whereby the bones in a subject are stabilized across the discontinuity.

The method also includes providing bone screws 12 with an external helical thread 13, applying torque to the threaded bone screws for anchoring into bone, and moving the compression ring linearly by application of equal and opposite forces.

Detailed embodiments of the instant invention are disclosed herein, however, it is to be understood that the disclosed embodiments are merely exemplary of the invention, which may be embodied in various forms. Therefore, specific functional and structural details disclosed herein are not to be interpreted as limiting, but merely as a basis for the claims and as a representation basis for teaching one skilled in the art to variously employ the present invention in virtually any appropriately detailed structure.

All patents and publications mentioned in this specification are indicative of the levels of those skilled in the art to which the invention pertains. All patents and publications are herein incorporated by reference to the same extent as if each individual publication was specifically and individually indicated to be incorporated by reference. It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

As used in this specification and the appended claims, the singular forms "a", "an", and "the" include plural referents unless the content clearly dictates otherwise.

As used in this specification and the appended claims, the term "or" is generally employed in its sense including "and/or" unless the content clearly dictates otherwise.

For purposes of this disclosure, "proximal" refers to the end closer to the device operator during use, and "distal" refers to the end farther from the device operator during use.

What is claimed is:

1. A bottom loading modular head assembly for stabilizing bones comprising:
    a bone screw having a first end and a second end, said first end constructed and arranged as a shank portion for penetrating securement to a bone, said second end constructed and arranged as a head portion; a connector for securing a rod to an anchored bone screw, said connector formed from a clamp securable to said head portion of said anchored bone screw wherein said clamp is inserted over said head portion of said anchored bone screw, said clamp having an elongated body with an exterior wall, said exterior wall including at least one annular bulge to provide a change in the external diameter of said exterior wall, at least one pin slot having a pin receiving portion constructed and arranged for receipt of a pin, said pin receiving portion comprising an expansion slot at a distal end and an opening at a proximal end forming a lip to allow uni-directional movement of said pin through said lip into a passageway; said passageway further comprising an expansion slot at an apex of said passageway;
    a rod slot extending across said exterior wall constructed and arranged to accept said rod; and, a compression ring surrounding said exterior wall, said compression ring comprises a pin receiving aperture which aligns with said pin receiving portion of said clamp when said assembly is in an unlocked position during installation;

wherein said clamp is linearly traversable along said exterior walls between a first or open position and a second or closed position by application of a force consisting of a linear force along a longitudinal axis of said clamp, whereby traversal of said clamp from said first position to said second position simultaneously causes (i) said pin to move past said lip portion and into shaft, said compressive forces prohibiting said pin from being pushed back into said pin receiving slot, and (ii) causes said clamp to cooperate with said at least one annular bulge to apply compressive forces to said clamp to immobilize the connections between said clamp and said rod and said clamp and said anchored bone screw.

2. The bottom loading modular head assembly for stabilizing bones of claim 1, wherein said clamp comprises a proximal end and a distal end, said proximal end defined by a U-shaped opening for receipt of a rod and said distal end defining an annulus.

3. The bottom loading modular head assembly for stabilizing bones of claim 1, wherein said has a length to allow variable positioning of said pin during installation.

4. The bottom loading modular head assembly for stabilizing bones of claim 1, wherein said compression ring includes at least one inner annular ridge constructed and arranged to engage said at least one annular bulge in an overlapping manner while said compression ring is in said second position, whereby engagement of said at least one bulge and said at least one ridge applies compressive forces to said clamp for immobilizing said clamp to said rod.

5. The bottom loading modular head assembly for stabilizing bones of claim 1, wherein said compression ring includes at least one inner annular ridge constructed and arranged to engage said at least one annular bulge in an overlapping manner while said compression ring is in said second position, whereby engagement of said at least one bulge and said at least one ridge applies compressive forces to said clamp for immobilizing said clamp to said head of the anchored bone screw.

6. The bottom loading modular head assembly for stabilizing bones of claim 1, wherein said at least one annular bulge is constructed and arranged to cooperate with said compression ring to apply compressive forces to said clamp for immobilizing at least one of said connections.

7. The bottom loading modular head assembly for stabilizing bones of claim 6, wherein the at least one annular bulge is constructed and arranged to cooperate with said compression ring while said compression ring is in said second position to immobilize the connection between said clamp and said bone screw said second bulge constructed and arranged to cooperate with said compression ring to immobilize the connection between said clamp while said compression ring is in said second position, whereby said compression ring may independently engage said first or said second bulges during translation thereof.

8. The bottom loading modular head assembly for stabilizing bones of claim 1, wherein said bone screw includes at least one helical thread for penetrating and engaging a bone and wherein said head portion is at least partially spherical in shape.

9. An apparatus comprising: a bone screw having a threaded shaft and a screw head; a connector having a clamp body with a receptacle sized to accommodate the head of an anchored bone screw wherein said clamp body is inserted over said head of said anchored bone screw; and, a compression ring around an exterior wall of the clamp body and movable along the exterior walls from an open position to a closed position, the compression ring including a pin receiving portion for receipt of a pin, said pin receiving portion comprising an expansion slot at a distal end and an opening at a proximal end forming a lip to allow uni-directional movement of said pin through said lip into a passageway, said passageway further comprising an expansion slot at an apex of said passageway;

a rod slot extending across said exterior wall constructed and arranged to accept a rod; a compression ring surrounding said exterior wall, said compression ring comprises a pin receiving aperture which aligns with said pin receiving portion of said clamp when said assembly is in an unlocked position during installation;

wherein said clamp is linearly traversable along said exterior walls between a first or open position and a second or closed position by application of a force consisting of a linear force along a longitudinal axis of said clamp, whereby traversal of said clamp from said first position to said second position simultaneously causes (i) said pin to move past said lip portion and into shaft, said compressive forces prohibiting said pin from being pushed back into said pin receiving slot, and (ii) causes said clamp to cooperate with at least one annular bulge to apply compressive forces to said clamp to immobilize the connections between said clamp and said rod and said clamp and said anchored bone screw.

10. The apparatus of claim 9, wherein the open position defined when the compression ring is moved towards the receptacle, wherein said connector is secured to an anchored bone screw by insertion of the head of the bone screw into the receptacle whereby the wall of the receptacle expands to allow receipt of the anchored bone screw head.

11. The apparatus of claim 9, wherein said receptacle includes slits to increase the radial flexibility of the wall as positioned within said compression ring.

12. The apparatus of claim 9, wherein said position of said compression ring with respect to said clamp body is adjustable when said compression ring is in the open position and is fixed with said compression ring is in the closed position.

13. The apparatus of claim 9, wherein said compression ring is pushed downwards, over said head of shank, said pin moving in an opposing direction into said pin receiving shaft, and said compression forces causing a narrowing of said lip of pin retention slot, thereby inhibiting said pin from moving past narrow gap.

14. The apparatus of claim 9, wherein said clamp body has annular bulges which engage annular ridges on the inside of said compression ring when said compression ring is in the closed position.

15. The apparatus of claim 9, wherein said rod slot has upper and lower longitudinal ridges to grip the rod.

* * * * *